(12) United States Patent
Mast et al.

(10) Patent No.: US 7,211,044 B2
(45) Date of Patent: May 1, 2007

(54) METHOD FOR MAPPING TEMPERATURE RISE USING PULSE-ECHO ULTRASOUND

(75) Inventors: T. Douglas Mast, Cincinnati, OH (US); Waseem Faidi, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 126 days.

(21) Appl. No.: 10/735,045

(22) Filed: Dec. 12, 2003

(65) Prior Publication Data

US 2004/0127791 A1 Jul. 1, 2004

Related U.S. Application Data

(63) Continuation-in-part of application No. 10/153,241, filed on May 22, 2002, now abandoned
(60) Provisional application No. 60/294,135, filed on May 29, 2001.

(51) Int. Cl.
*A61B 8/00* (2006.01)

(52) U.S. Cl. .................................................. 600/439
(58) Field of Classification Search ......... 600/437–439, 600/443, 447; 601/2–4; 374/46, 102, 117, 374/119, 120
See application file for complete search history.

(56) References Cited

U.S. PATENT DOCUMENTS

| | | | |
|---|---|---|---|
| 3,779,234 A | 12/1973 | Eggleton et al. |
| 4,315,514 A | 2/1982 | Drewes et al. |
| 4,323,077 A | 4/1982 | Smith |
| 4,484,569 A | 11/1984 | Driller et al. |
| 4,646,756 A | 3/1987 | Watnough et al. |
| 4,757,820 A | 7/1988 | Itoh |
| 4,787,394 A | 11/1988 | Ogura |
| 4,818,954 A | 4/1989 | Flachenecker et al. |
| 4,858,613 A | 8/1989 | Fry et al. |
| 4,932,414 A | 6/1990 | Coleman et al. |
| 4,951,653 A | 8/1990 | Fry et al. |
| 4,955,365 A | 9/1990 | Fry et al. |
| 4,955,366 A | 9/1990 | Uchiyama et al. |
| 4,960,107 A | 10/1990 | Aida et al. |
| 4,984,575 A | 1/1991 | Uchiyama et al. |

(Continued)

FOREIGN PATENT DOCUMENTS

| | | |
|---|---|---|
| EP | 0897696 A1 | 2/1999 |
| JP | 9098980 | 4/1997 |
| JP | 10-14967 | 1/1998 |

(Continued)

OTHER PUBLICATIONS

Maass–Moreno, Roberto et al., "Noninvasive temperature estimation in tissue via ultrasound echo–shifts. Part I. Analytical Study". J. Accoust. Soc. Am., vol. 100, No. 4, Pt. 1, Oct. 1998, pp. 2514–2521.

(Continued)

*Primary Examiner*—Francis J. Jaworski

(57) ABSTRACT

A method for measuring the temperature rise in anatomical tissue as a result of ultrasound treatment. A first ultrasound signal is obtained prior to treating the anatomical tissue, then a second ultrasound signal is obtained after the tissue is treated. Complex analytic signals are computed from the first and second ultrasound signals, then the depth-dependent delay is computed from the complex analytic signals. An echo strain map is generated from the slope of the depth-dependent delay. The echo strain map is used to estimate the amount of temperature rise from the first ultrasound signal to the second ultrasound signal. An image may then be created showing where temperature rise is occurring in the anatomical tissue.

21 Claims, 9 Drawing Sheets

U.S. PATENT DOCUMENTS

| | | |
|---|---|---|
| 4,986,275 A | 1/1991 | Ishida et al. |
| 5,005,580 A | 4/1991 | Okazaki |
| RE33,590 E | 5/1991 | Dory |
| 5,015,929 A | 5/1991 | Cathignol et al. |
| 5,036,855 A | 8/1991 | Fry et al. |
| 5,042,486 A | 8/1991 | Pfeiler et al. |
| 5,054,470 A | 10/1991 | Fry et al. |
| 5,065,740 A | 11/1991 | Itoh |
| 5,031,626 A | 12/1991 | Hassler et al. |
| 5,078,144 A | 1/1992 | Sekino et al. |
| 5,080,101 A | 1/1992 | Dory |
| 5,080,102 A | 1/1992 | Dory |
| 5,095,906 A | 3/1992 | Ema |
| 5,095,907 A | 3/1992 | Kudo et al. |
| 5,143,073 A | 9/1992 | Dory |
| 5,143,074 A | 9/1992 | Dory |
| 5,148,809 A | 9/1992 | Bielgeleisen-Knight et al. |
| 5,149,319 A | 9/1992 | Unger |
| 5,150,711 A | 9/1992 | Dory |
| 5,150,712 A | 9/1992 | Dory |
| 5,158,070 A | 10/1992 | Dory |
| 5,158,071 A | 10/1992 | Umemura et al. |
| 5,203,333 A | 4/1993 | Nomura |
| 5,209,221 A | 5/1993 | Riedlinger |
| 5,240,005 A | 8/1993 | Viebach |
| 5,295,484 A | 3/1994 | Marcus et al. |
| 5,304,115 A | 4/1994 | Pflueger et al. |
| 5,311,869 A | 5/1994 | Okazaki |
| 5,345,940 A | 9/1994 | Seward et al. |
| 5,354,258 A | 10/1994 | Dory |
| 5,391,140 A | 2/1995 | Schaetzle et al. |
| 5,391,197 A | 2/1995 | Burdette et al. |
| 5,398,690 A | 3/1995 | Batten et al. |
| 5,402,792 A | 4/1995 | Kimura |
| 5,409,002 A | 4/1995 | Pell |
| 5,421,338 A | 6/1995 | Crowley et al. |
| 5,431,663 A | 7/1995 | Carter |
| 5,435,304 A | 7/1995 | Oppelt et al. |
| 5,435,311 A | 7/1995 | Umemura et al. |
| 5,443,069 A | 8/1995 | Schaetzle |
| 5,448,994 A | 9/1995 | Iinuma |
| 5,471,988 A | 12/1995 | Fujio et al. |
| 5,474,071 A | 12/1995 | Chapelon et al. |
| 5,485,839 A | 1/1996 | Aida et al. |
| 5,492,126 A | 2/1996 | Hennige et al. |
| 5,520,188 A | 5/1996 | Hennige et al. |
| 5,522,869 A | 6/1996 | Burdette et al. |
| 5,524,620 A | 6/1996 | Rosenschein |
| 5,526,815 A | 6/1996 | Granz et al. |
| 5,526,822 A | 6/1996 | Burbank et al. |
| 5,540,656 A | 7/1996 | Pflueger et al. |
| 5,545,195 A | 8/1996 | Lennox et al. |
| 5,549,638 A | 8/1996 | Burdette |
| 5,553,618 A * | 9/1996 | Suzuki et al. ............... 600/411 |
| 5,569,241 A | 10/1996 | Edwards |
| 5,571,088 A | 11/1996 | Lennox et al. |
| 5,573,497 A | 11/1996 | Chapelon |
| 5,575,772 A | 11/1996 | Lennox |
| 5,575,789 A | 11/1996 | Bell et al. |
| 5,582,588 A | 12/1996 | Sakurai et al. |
| 5,588,432 A | 12/1996 | Crowley |
| 5,590,657 A | 1/1997 | Cain et al. |
| 5,596,991 A | 1/1997 | Tanaka |
| 5,601,526 A | 2/1997 | Chapelon et al. |
| 5,603,326 A | 2/1997 | Richter |
| 5,606,975 A | 3/1997 | Liang et al. |
| 5,620,479 A | 4/1997 | Diederich |
| 5,624,382 A | 4/1997 | Oppelt et al. |
| 5,628,743 A | 5/1997 | Cimino |
| 5,643,179 A | 7/1997 | Fujimoto |
| 5,649,547 A | 7/1997 | Ritchart et al. |
| 5,657,760 A * | 8/1997 | Ying et al. ................... 600/439 |
| 5,665,054 A | 9/1997 | Dory |
| 5,666,954 A | 9/1997 | Chapelon et al. |
| 5,676,692 A | 10/1997 | Sanghvi et al. |
| 5,687,729 A | 11/1997 | Schaetzle |
| 5,694,936 A | 12/1997 | Fujimoto et al. |
| 5,697,897 A | 12/1997 | Buchholtz et al. |
| 5,699,804 A | 12/1997 | Rattner |
| 5,699,805 A | 12/1997 | Seward et al. |
| 5,703,922 A | 12/1997 | Rattner |
| 5,720,287 A | 2/1998 | Chapelon et al. |
| 5,722,411 A | 3/1998 | Suzuki et al. |
| 5,728,062 A | 3/1998 | Brisken |
| 5,733,315 A | 3/1998 | Burdette et al. |
| 5,735,280 A | 4/1998 | Sherman et al. |
| 5,735,796 A | 4/1998 | Granz et al. |
| 5,738,635 A | 4/1998 | Chapelon et al. |
| 5,743,862 A | 4/1998 | Izumi |
| 5,743,863 A | 4/1998 | Chapelon |
| 5,746,224 A | 5/1998 | Edwards |
| 5,759,162 A | 6/1998 | Oppelt et al. |
| 5,762,066 A | 6/1998 | Law et al. |
| 5,769,086 A | 6/1998 | Ritchart et al. |
| 5,769,790 A | 6/1998 | Watkins et al. |
| 5,776,092 A | 7/1998 | Farin et al. |
| 5,788,636 A | 8/1998 | Curley |
| 5,800,379 A | 9/1998 | Edwards |
| 5,807,308 A | 9/1998 | Edwards |
| 5,810,742 A | 9/1998 | Pearlman |
| 5,817,021 A | 10/1998 | Reichenberger |
| 5,817,049 A | 10/1998 | Edwards |
| 5,820,580 A | 10/1998 | Edwards et al. |
| 5,823,962 A | 10/1998 | Schaetzle et al. |
| 5,836,896 A | 11/1998 | Rosenschein |
| 5,840,022 A | 11/1998 | Richter |
| 5,840,031 A | 11/1998 | Crowley |
| 5,860,974 A | 1/1999 | Abele |
| 5,873,828 A | 2/1999 | Fujio et al. |
| 5,873,845 A | 2/1999 | Cline et al. |
| 5,873,902 A | 2/1999 | Sanghvi et al. |
| 5,882,302 A | 3/1999 | Driscoll, Jr. et al. |
| 5,893,835 A | 4/1999 | Witt |
| 5,895,356 A | 4/1999 | Andrus et al. |
| 5,897,495 A | 4/1999 | Aida et al. |
| 5,928,169 A | 7/1999 | Schatzle et al. |
| 5,938,600 A | 8/1999 | Van Vaals et al. |
| 5,938,608 A | 8/1999 | Bieger et al. |
| 5,944,663 A | 8/1999 | Kuth et al. |
| 5,964,755 A | 10/1999 | Edwards |
| 5,976,105 A | 11/1999 | Marcove |
| 5,984,881 A | 11/1999 | Ishibashi et al. |
| 5,984,882 A | 11/1999 | Rosenschein et al. |
| 5,993,389 A | 11/1999 | Driscoll, Jr. et al. |
| 6,004,269 A | 12/1999 | Crowley et al. |
| 6,007,499 A | 12/1999 | Martin et al. |
| 6,013,031 A | 1/2000 | Mendlein et al. |
| 6,024,718 A | 2/2000 | Chen et al. |
| 6,024,740 A | 2/2000 | Lesh et al. |
| 6,039,689 A | 3/2000 | Lizzi |
| 6,042,556 A | 3/2000 | Beach et al. |
| 6,050,943 A | 4/2000 | Slayton et al. |
| 6,053,868 A | 4/2000 | Geistert et al. |
| 6,059,731 A | 5/2000 | Seward et al. |
| 6,063,050 A | 5/2000 | Manna et al. |
| 6,066,123 A | 5/2000 | Li et al. |
| 6,071,238 A | 6/2000 | Chapelon et al. |
| 6,071,239 A | 6/2000 | Cribbs et al. |
| 6,071,279 A | 6/2000 | Whayne et al. |
| 6,083,159 A | 7/2000 | Driscoll, Jr. et al. |
| 6,086,535 A | 7/2000 | Ishibashi et al. |

| | | | |
|---|---|---|---|
| 6,088,613 | A | 7/2000 | Unger |
| 6,106,470 | A | 8/2000 | Geiser |
| 6,106,517 | A | 8/2000 | Zupkas |
| 6,113,558 | A | 9/2000 | Rosenschein et al. |
| 6,117,101 | A | 9/2000 | Diederich et al. |
| 6,135,971 | A | 10/2000 | Hutchinson et al. |
| 6,149,598 | A | 11/2000 | Tanaka |
| 6,156,029 | A | 12/2000 | Mueller |
| 6,159,207 | A | 12/2000 | Yoon |
| 6,193,709 | B1 | 2/2001 | Miyawaki et al. |
| 6,206,843 | B1 | 3/2001 | Voni et al. |
| 6,210,330 | B1 | 4/2001 | Tepper |
| 6,221,014 | B1 | 4/2001 | Bauer |
| 6,246,898 | B1 | 6/2001 | Vesely et al. |
| 6,266,552 | B1 | 7/2001 | Slettenmark |
| 6,340,352 | B1 | 1/2002 | Okada |
| 6,352,532 | B1 | 3/2002 | Kramer et al. |
| 6,371,903 | B1 | 4/2002 | Blanc et al. |
| 6,425,867 | B1 | 7/2002 | Vaezy et al. |
| 6,461,314 | B1 | 10/2002 | Pant et al. |
| 6,488,626 | B1 * | 12/2002 | Lizzi et al. .............. 600/437 |
| 6,533,726 | B1 | 3/2003 | Lizzi |
| 6,540,700 | B1 | 4/2003 | Fujimoto |
| 6,562,033 | B2 | 5/2003 | Shah |
| 6,575,969 | B1 | 6/2003 | Rittman et al. |
| 6,635,054 | B2 | 10/2003 | Fjield |
| 6,659,949 | B1 | 12/2003 | Lang et al. |
| 6,702,745 | B1 | 3/2004 | Smythe |
| 6,726,677 | B1 | 4/2004 | Flaherty |
| 2003/0120306 | A1 | 6/2003 | Burbank et al. |
| 2004/0041880 | A1 | 3/2004 | Pharmasonics |

FOREIGN PATENT DOCUMENTS

| | | |
|---|---|---|
| WO | WO 97/29709 A | 8/1997 |
| WO | WO 98/58588 A1 | 12/1998 |
| WO | WO 99/33500 A | 7/1999 |
| WO | WO 01/34018 A2 | 5/2001 |
| WO | WO 01/43641 A | 6/2001 |
| WO | WO 01/45550 A2 | 6/2001 |
| WO | WO 01/97702 A | 12/2001 |

OTHER PUBLICATIONS

Maass–Moreno, Roberto et al., "Noninvasive temperature estimation in tissue via ultrasound echo–shifts. Part II. In vitro study". J. Accoust. Soc. Am., vol. 100, No. 4, Pt. 1, Oct. 1998, pp. 2522–2530.

Seip, Ralf et al., "Noninvasive Real–Time Multipoint Temperature Control for Ultrasound Phased Array Treatments". IEEE Transactions on ultrasonics, ferroelectrics, and frequency control. vol. 43, No. 6, Nov. 1996. pp. 1063–1073.

Simon, Claudio et al., "Two–Dimensional Temperature Estimation Using Diagnostic Ultrasound". IEE Transactions on ultrasonics, ferroelectrics, and frequency control. vol. 45, No. 4, Jul. 1998. pp. 1088–1099.

International Preliminary Examination Report dated Mar. 30, 2004 for corresponding International patent application PCT/US02/16695.

EPO Search Report dated Jun. 6, 2006 for related patent application, Application No. EP 02 73 9439.

EPO Search Report dated Jun. 8, 2006 for related patent application, Application No. EP 02 74 1739.

EPO Search Report dated Jun. 7, 2006 for related patent application, Application No. EP 02 73 1924.

EPO Search Report dated Aug. 31, 2006 for related patent application, Application No. EP 02 73 7136.

EPO Search Report dated Aug. 25, 2006, for related patent application, Application No. EP 02 73 9440.

EPO Search Report dated Oct. 11, 2005 for corresponding patent application, PCT Patent Application No. PCT/US04/41799.

Maass–Moreno, Roberto et al., "Noninvasive temperature estimation in tisue via ultrasound echo–shifts. Part 1. Analytical study", J. Acoust. Soc. Am., vol. 100, No. 4, Pt. 1, Oct. 1996, pp. 2514–2521.

* cited by examiner

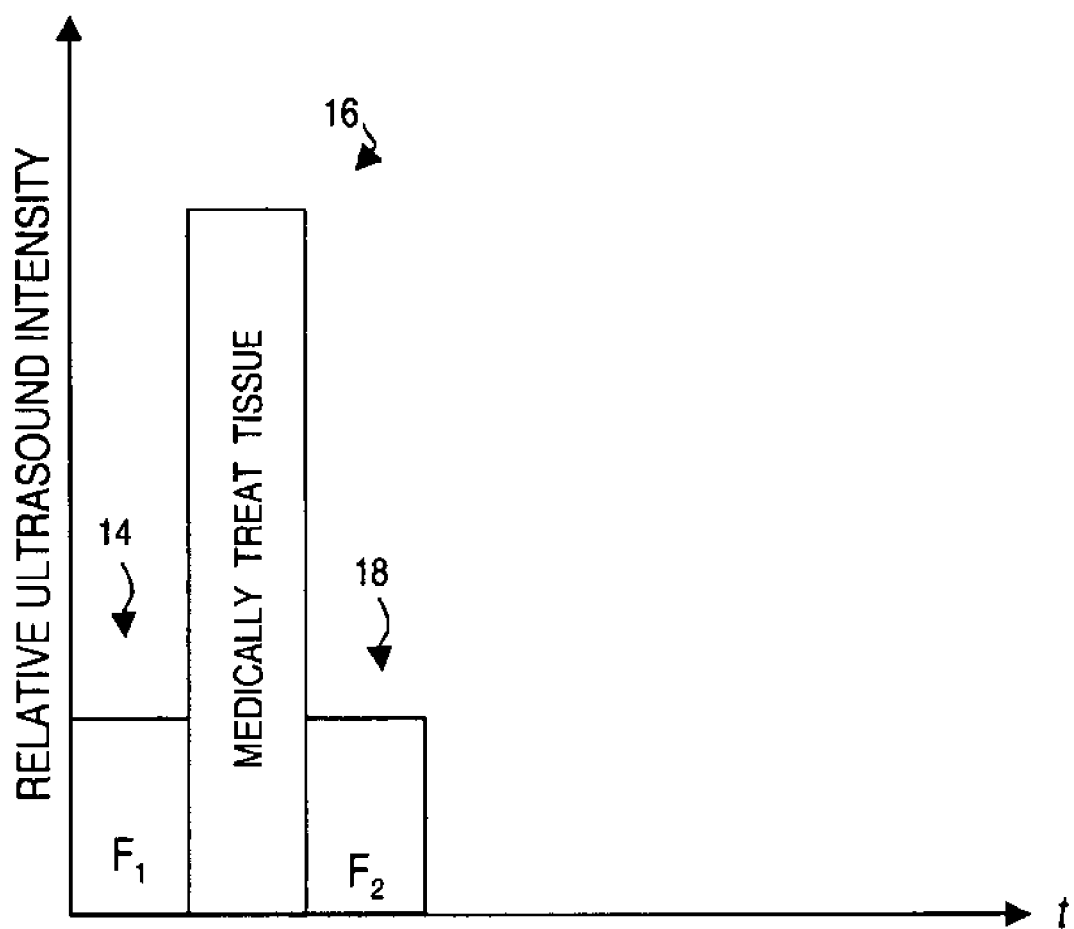
_Fig. 3_

US 7,211,044 B2

METHOD FOR MAPPING TEMPERATURE RISE USING PULSE-ECHO ULTRASOUND

RELATED APPLICATIONS

This is a continuation-in-part of application Ser. No. 10/153,241, filed May 22, 2002 now abandoned, which claims priority to U.S. Provisional Application Ser. No. 60/294,135 filed May 29, 2001. The entire disclosures are incorporated herein by reference.

FIELD OF THE INVENTION

The present invention relates generally to ultrasound, and more particularly, to a method for measuring temperature rise using pulse-echo ultrasound waves.

BACKGROUND OF THE INVENTION

Ultrasound medical systems and methods include ultrasound imaging of anatomical tissue to identify tissue for medical treatment. Ultrasound may also be used to medically treat and destroy unwanted tissue by heating the tissue. Imaging is done using low-intensity ultrasound waves, while medical treatment is performed with high-intensity ultrasound waves. High-intensity ultrasound waves, when focused at a focal zone a distance away from the ultrasound source, will substantially medically affect tissue in the focal zone. However, the high-intensity ultrasound will not substantially affect patient tissue outside the focal zone, such as tissue located between the ultrasound source and the focal zone. Other treatment regimes of interest include unfocused high-intensity ultrasound wherein the ultrasound energy is distributed over a relatively broad region of tissue rather than being generally concentrated within a focal zone.

Ultrasound waves may be emitted and received by a transducer assembly. The transducer assembly may include a single transducer element, or an array of elements acting together, to image the anatomical tissue and to ultrasonically ablate identified tissue. Transducer elements may employ a concave shape or an acoustic lens to focus or otherwise direct ultrasound energy. Transducer such arrays may include planar, concave or convex elements to focus ultrasound energy. Further, array elements may be electronically or mechanically controlled to steer and focus the ultrasound waves emitted by the array to a focal zone to provide three-dimensional medical ultrasound treatment of anatomical tissue. In some treatments the transducer is placed on the surface of the tissue for imaging and/or treatment of areas within the tissue. In other treatments the transducer is surrounded with a balloon which is expanded to contact the surface of the tissue by filling the balloon with a fluid such as a saline solution to provide acoustic coupling between the transducer and the tissue.

Examples of ultrasound medical systems and methods include: deploying an end effector having an ultrasound transducer outside the body to break up kidney stones inside the body; endoscopically inserting an end effector having an ultrasound transducer into the rectum to medically destroy prostate cancer; laparoscopically inserting an end effector having an ultrasound transducer into the abdominal cavity to destroy a cancerous liver tumor; intravenously inserting a catheter end effector having an ultrasound transducer into a vein in the arm and moving the catheter to the heart to medically destroy diseased heart tissue; and interstitially inserting a needle end effector having an ultrasound transducer into the tongue to medically destroy tissue to reduce tongue volume as a treatment for snoring. Methods for guiding an end effector to the target tissue include x-rays, Magnetic Resonance Images ("MRI") and images produced using the ultrasound transducer itself.

Low-intensity ultrasound energy may be applied to unexposed subdermal anatomical tissue for the purpose of examining the tissue. Ultrasound pulses are emitted, and returning echos are measured to determine the characteristics of the unexposed subdermal tissue. Variations in tissue structure and tissue boundaries have varying acoustic impedances, resulting in variations in the strength of ultrasound echos. A common ultrasound imaging technique is known in the art as "B-Mode" wherein either a single ultrasound transducer is articulated or an array of ultrasound transducers is moved or electronically scanned to generate a two-dimensional image of an area of tissue. The generated image is comprised of a plurality of pixels, each pixel corresponding to a portion of the tissue area being examined. The varying strength of the echos is preferably translated to a proportional pixel brightness. A cathode ray tube, computer monitor or liquid crystal display can be used to display a two-dimensional pixellated image of the tissue area being examined.

When high-intensity ultrasound energy is applied to anatomical tissue, significant beneficial physiological effects may result. For example, undesired anatomical tissue may be ablated by heating the tissue with high-intensity ultrasound energy. By focusing the ultrasound energy at one or more specific focusing zones within the tissue, thermal effects can be confined to a defined region that may be remote from the ultrasound transducer. The use of high-intensity focused ultrasound to ablate tissue presents many advantages, including: reduced patient trauma and pain; elimination of the need for some surgical incisions and stitches; reduced or obviated need for general anesthesia; reduced exposure of internal tissue; reduced risk of infection and other complications; avoidance of damage to non-targeted tissue; lack of harmful cumulative effects from the ultrasound energy on the surrounding non-target tissue; reduced treatment costs; minimal blood loss; and the ability for ultrasound treatments to be performed at non-hospital sites and/or on an out-patient basis.

Ultrasound treatment of anatomical tissue may involve the alternating use of both low-intensity imaging ultrasound and high-intensity treatment ultrasound. During such treatment, imaging is first performed to identify and locate the tissue to be treated. The identified tissue is then medically treated with high-intensity ultrasound energy, such as for the purpose of destroying the tissue. After a period of exposure to high-intensity ultrasound, a subsequent image of the tissue is generated using low-intensity ultrasound energy to determine the results of the ultrasound treatment and provide visual guidance to the user to aid in subsequent treatments. This process of applying low-energy ultrasound to assist in guiding the position and focal point of the transducer, followed by high-energy ultrasound to ablate the undesired anatomical tissue, may continue until the undesired tissue has been completely ablated.

In addition to imaging, monitoring of the temperature of the tissue being treated is desirable so that the tissue being treated, as well as the delivered treatment, can be readily visualized and controlled. For example, temperature monitoring is essential for hyperthermia treatments wherein tissue is exposed to ultrasound for the purpose of raising the temperature of the tissue. Hyperthermia treatments have been shown to be effective in the treatment of cancerous tumors, which are known to be more sensitive to heat than healthy tissue. Temperature monitoring is also useful for high-intensity ultrasound treatment of tissue, such as ablation, since the temperature of the tissue provides an indication of the extent and spatial distribution of the treatment.

The temperature of the tissue may be measured directly, such as with a thermocouple array. However, this arrangement is not desirable for several reasons. First, the thermocouple array must be placed into the region being treatment. This may require invasive placement of the array, thereby eliminating the non-invasive treatment advantages offered by ultrasound. In addition, the thermocouple array may have a relatively slow response time, providing the operator with delayed feedback regarding the status of the treatment.

Various non-invasive temperature-monitoring methods have been developed to overcome the drawbacks of thermocouple arrays. For example, magnetic resonance imaging ("MRI") is used in the art to noninvasively measure temperature rises in vivo. However, MRI feedback requires an apparatus separate from the ultrasound treatment apparatus to provide the temperature measurement. As a result, MRI-assisted ultrasound methods are expensive and cumbersome, making such treatment impractical for routine use in surgical treatments.

The prior art has suggested using ultrasound waves to measure temperature. Previous studies have shown that temperature rises in tissue cause local thermal expansion and sound speed changes, which can be estimated from perturbations of ultrasonic echo signals. Since the travel time of an ultrasonic echo depends on both the path length (which is changed by any thermal expansion) and sound speed (which depends on temperature), temperature changes in tissue being treated cause measurable alterations to echo travel times. By estimation and further processing of these travel times, temperature rises can be approximately mapped. This arrangement is highly desirable, since heating effects of ultrasound treatment may be measured using inexpensive, portable, and unobtrusive ultrasound apparatus. For configurations in which therapy and monitoring are performed using the same ultrasound probe, this approach is particularly desirable, since a temperature map may be automatically co-registered with the therapeutic ultrasound beams.

Available approaches to pulse-echo temperature mapping have employed cross-correlation of ultrasound echo signals to estimate changes in travel time (i.e., delay) for each pixel of an image, before and after heating. These travel-time maps are then smoothed and differentiated by signal processing to obtain maps of the echo strain, which is assumed to be proportional to the temperature rise of the tissue being treated. Repetition of this process can follow incremental temperature rises associated with prolonged heating. These approaches suffer from several drawbacks, including low spatial resolution and high artifactual content. Since many time-delay estimation steps are needed to build up a temperature image, these approaches are also computationally inefficient.

There is a need for a method of measuring the temperature rise of tissue being treated by ultrasound that is noninvasive. There is a further need for method of monitoring temperature rise that is not expensive and is not cumbersome. There is a still further need for a method of monitoring temperature measurement that has relatively high spatial resolution and relatively low artifactual content, and is computationally efficient.

SUMMARY OF THE INVENTION

The present invention overcomes the limitations of the known art by estimating the time-dependent delay between two sets of narrow-band ultrasound signals. The travel time of a first signal is measured prior to treating anatomical tissue, then the travel time of a second signal is measured after the tissue is treated. The change in travel time between the first and second signals is used to generate a complete two-dimensional delay map from several two-dimensional multiplication and fast Fourier transform operations, rather than creating a map from a large quantity of individual time delay estimation steps. As a result, temperature maps can be generated more quickly as compared to prior methods. In addition, temperature maps generated using the present invention have fewer artifacts.

BRIEF DESCRIPTION OF THE DRAWINGS

Further features of the present invention will become apparent to those skilled in the art to which the present invention relates from reading the following specification with reference to the accompanying drawings, in which:

FIG. 3 illustrates the relative amplitude and timing of ultrasound image frames and ultrasound treatments according to an embodiment of the present invention;

DETAILED DESCRIPTION

It is well-known that the travel time of an ultrasound wave varies with the path length. The path length may vary in anatomic tissue due to thermal expansion of the tissue as a result of therapeutic ultrasound treatment, such as hyperthermia and ablation. Further, the travel time of an ultrasound wave varies with the speed of the ultrasound wave, which is a function of path temperature. Thus, changes in ultrasound wave travel times may be used to estimate temperature rise.

Figure 1A:
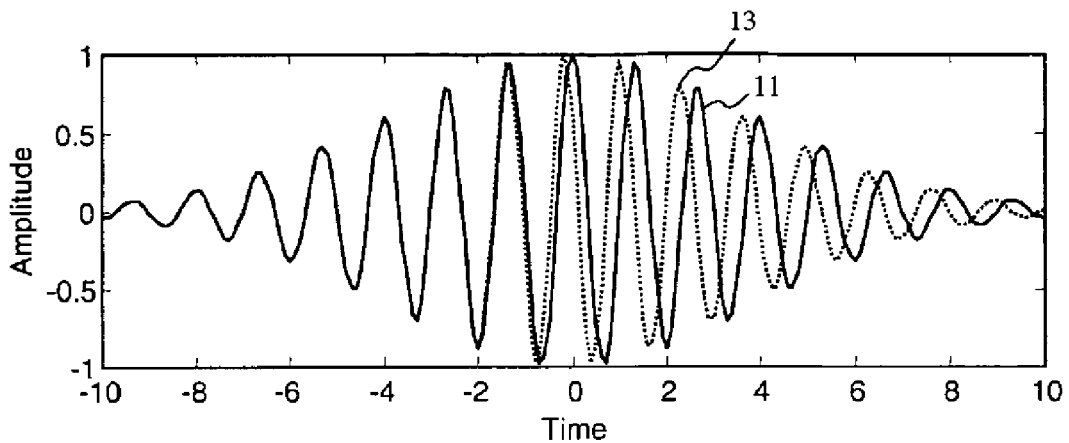
FIG. 1A illustrates ultrasound signals before and after an ultrasound medical treatment.
Figure 1B:
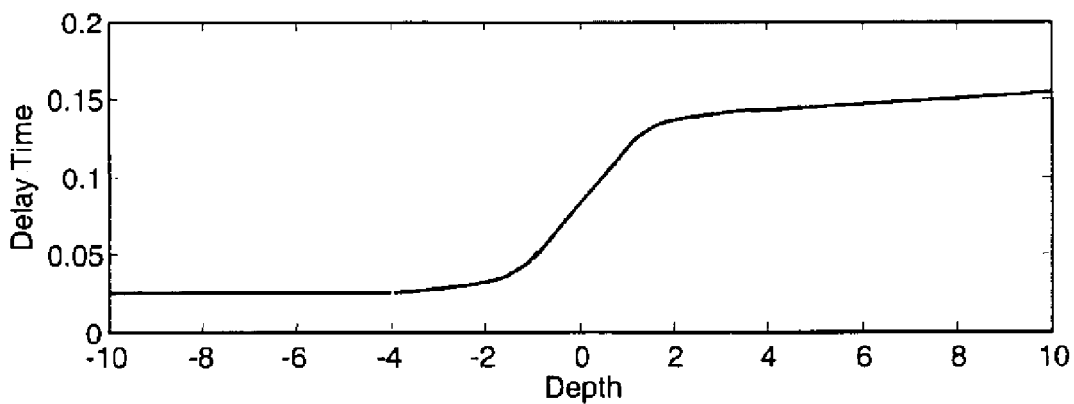
FIG. 1B is a graph of changes in travel time for ultrasound echo signals.
Figure 1C:
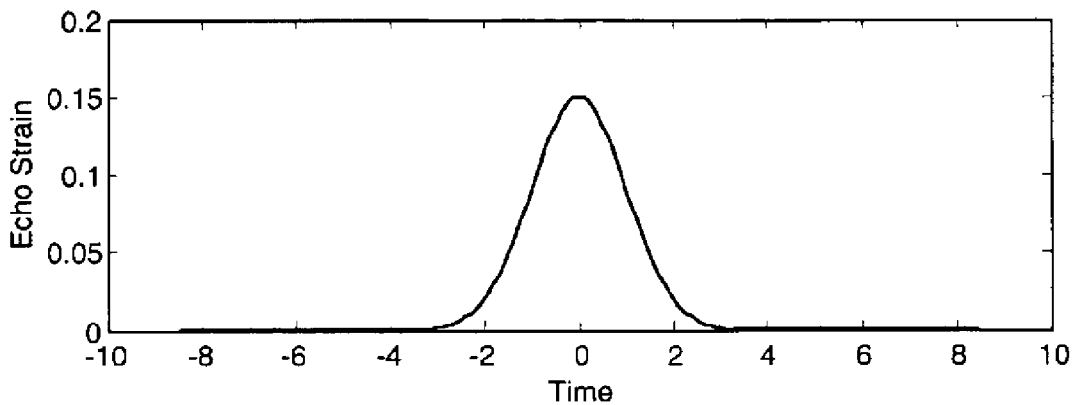
FIG. 1C is a graph of ultrasound echo strain.

FIGS. 1A–1C provide an overview of a method for mapping temperature rise according to an embodiment of the present invention. FIG. 1A generally illustrates a first ultrasound signal 11 returning to an ultrasound transducer (not shown) before treatment of a region of tissue, while ultrasound signal 13 represents an ultrasound signal returning to the ultrasound transducer after treatment of the tissue. The relative delay between ultrasound echos returning to an ultrasound transducer, measured before and after treatment, is estimated as a function of depth, as shown in the graph of FIG. 1B. The slope of the depth-dependent delay represents echo strain, as illustrated in FIG. 1C. Echo strain is defined as the slope (time derivative) of the time-dependent (equivalent to depth-dependent) signal delay, as shown in FIGS. 1A–1C. The amount of echo strain is proportional to the temperature rise of the heated region, as can be seen by comparing FIGS. 1A–1C.

Figure 2:
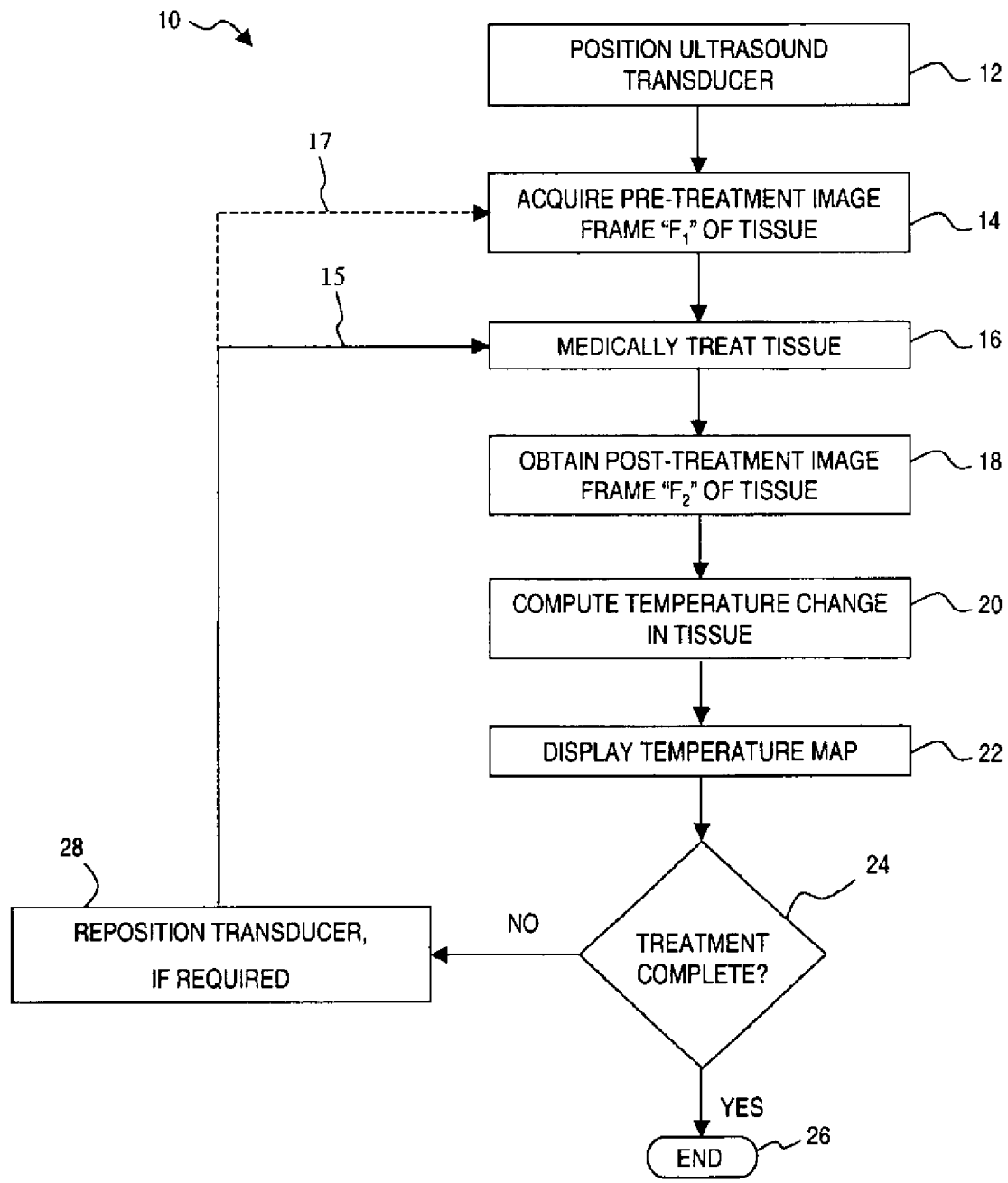
FIG. 2 is a flow diagram providing an overview of an ultrasound treatment method according to an embodiment of the present invention.

A flow diagram of the general arrangement of an ultrasound treatment method 10 according to an embodiment of the present invention is shown in FIG. 2. The method begins at step 12 by positioning proximate the tissue to be medically treated a transducer capable of transmitting and receiving ultrasound signals. At step 14 a low-intensity imaging ultrasound signal, such as a B-Mode signal, is emitted from the transducer and the reflected signals are collected to form a pre-treatment image frame "$F_1$." For each frame, a number of A-lines of raw echo signal radio frequency ("RF") data are obtained; a line number corresponds to azimuthal position and signal time corresponds to depth. It is understood that the terms "image" and "imaging" comprise, without limitation, any means for creating a visually-perceivable image that may be displayed, for example, on a monitor, screen or display, or printed. The terms "image" and "imaging" may further comprise image information that may be used by electronic devices such as computers without being displayed in visually perceivable form.

Medical treatment begins at step 16 by emitting an ultrasound signal from the transducer. The term "medical treatment" as used herein may comprise several types of ultrasound treatment. For example, the medical treatment may be a relatively low-intensity ultrasound signal, causing a small temperature rise in the tissue (such as 1° C. or less) that does not alter the tissue. Low-intensity ultrasound medical treatment is relevant for targeting of tissue for higher-intensity medical treatment, wherein the low-intensity ultrasound signal creates a small temperature rise that may be imaged to ensure that the desired region of tissue is targeted by the ultrasound beam. After targeting is confirmed, the amplitude of the ultrasound signal may be raised to a higher intensity. The high-intensity ultrasound signal may be used to administer a hyperthermia treatment or to ablate the tissue.

After a portion of the tissue has been medically treated, a post-treatment image frame "$F_2$" is generated at step 18. Information gathered from the pre-treatment and post-treatment image frames is then used at step 20 to compute the change in the temperature of the tissue being treated. The results of the temperature computations may then be displayed at step 22. The display may be in any convenient form to aid the user in interpreting the temperature data. For example, the display may be in the form of textual data relating to the temperature of the treated tissue. The display may also include a graphical presentation wherein colors are used to represent temperatures and temperature gradients of the treated tissue. If treatment is complete at step 24, the method is ended at step 26. However, if the tissue requires additional treatment, the transducer may be re-positioned if desired at step 28 using the image of step 18 as a guide. The method then returns to step 16 to again medically treat the tissue. The post-treatment image frame from the first treatment may be used as a pre-treatment image for the second treatment, as shown by arrow 15 of FIG. 2. Alternatively, a new pre-treatment image 14 may be obtained, as indicated by arrow 17 of FIG. 2.

FIG. 3 illustrates the method of FIG. 2 in relation to a time scale t. The B-Mode image scans 14, 18 are represented as frames $F_1$, $F_2$ respectively. For each frame, a number of A-lines of raw echo signal data are obtained, the number of each line corresponding to azimuthal position while signal time corresponds to depth.

Figure 4:
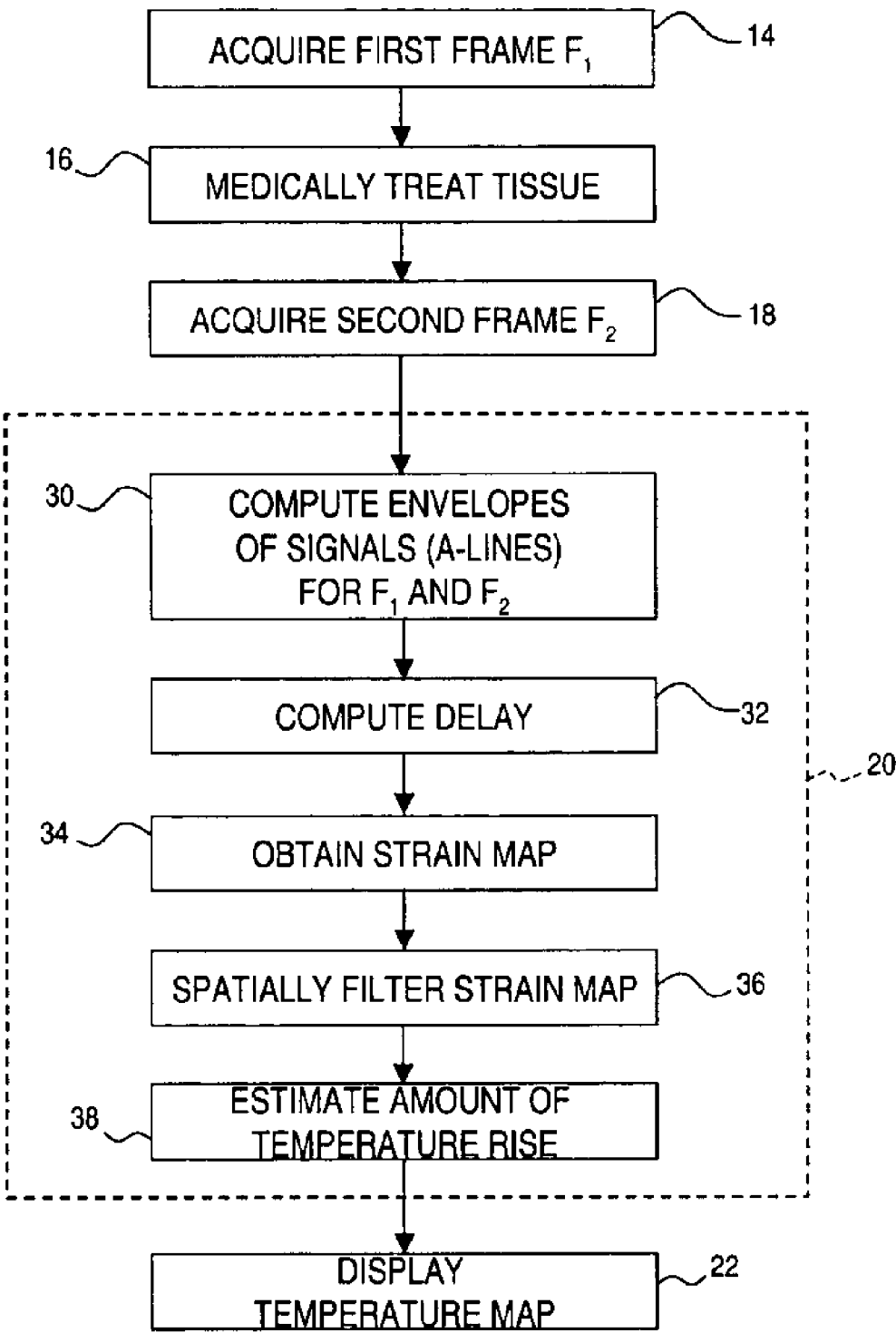
FIG. 4 is a flow diagram of a method for mapping temperature rise using pulse-echo ultrasound according to an embodiment of the present invention.

Referring now to FIG. 4 in combination with FIG. 3, a method for estimating the temperature rise of anatomical tissue in response to medical treatment according to an embodiment of the present invention is depicted. An ultrasound transducer is positioned proximate the anatomical tissue, then at step 14 a first image frame $F_1$ (illustrated in FIG. 4) is acquired. The frame may be stored electronically, such as in a computer, magnetic media and solid-state memory. The tissue may then be medically treated such as by hyperthermia or ablating it with high-intensity ultrasound waves, as at step 16. A second image frame $F_2$ is then acquired at step 18 and electronically stored. For each frame, a number of A-lines of raw echo signal data are obtained. A line number assigned to each A-line corresponds to azimuthal position, whereas signal time corresponds to depth. The raw echo signals of frames $F_1$ and $F_2$ may be processed at step 30, such as to obtain complex analytic signals by means of a conventional Hilbert transformation. For small temperature rises the echo signal $p_1$ obtained after treatment differs from $p_0$, the echo signal obtained prior to treatment, only by a time-dependent delay. Echo signals $p_0$ and $p_1$ may be expressed below in Equations 1 and 2:

$$p_0(t) = a_0(t)e^{-i\varpi_0 t} \qquad \text{Equation 1}$$

$$p_1(t) = a_0(t + \delta t)e^{-i\varpi_0(t+\delta t)} \qquad \text{Equation 2}$$

where $a_0$ is the complex amplitude envelope, $\omega_0$ is a nominal center frequency of the signals, and $\delta t$ is the time-dependent delay.

At step 32 the delay $\delta t$ is estimated as a function of time as follows. The processed echo signal $p_0$ from frame $F_1$ is multiplied by the conjugate of $p_1$ from frame $F_2$. This conjugate product is spatially filtered to yield a spatial map of a zero-lag cross-correlation between $F_1$ and $F_2$. For the signals of Equations 1 and 2, a windowed zero-lag cross-correlation may be expressed by Equation 3 for a window centered at time $t_0$:

$$R_{01}(0, t_0) = e^{-i\omega_0 \delta t} \int_{-\infty}^{\infty} w(t - t_0) a_0 * (t + \delta t) dt \qquad \text{Equation 3}$$

Since this zero-lag cross-correlation takes the form of a convolution between the conjugate product of the echoes and a windowing function w, this cross-correlation can be computed efficiently for all times $t_0$, using the fast Fourier transform. This eliminates the need for computing separate cross-correlations for multiple windows spanning the region of interest.

The depth-dependent delay is then given by the phase of the zero-lag cross-correlation $R_{01}(0,t_0)$:

$$\delta t(t) \approx -\frac{\arg\langle R_{01}(0, t)\rangle}{\omega_0} \qquad \text{Equation 4}$$

The phase of the conjugate product is computed for all the A-lines, using techniques such as appropriate phase unwrapping, to efficiently estimate the azimuth- and depth-dependent delay $\delta t$ between the echo signals of the two frames using Equation 4. At step 34 the relative strain between the two frames is computed as the derivative of this signal delay, taken along the time/range direction. This relative strain (termed an "echo strain map" herein) can be computed by known methods, such as finite differences. The echo strain map represents the slope of the depth-dependent delay and assumes a linear relationship between echo strain and temperature rise.

At step 36, the echo strain map can optionally be spatially filtered to reduce any strain artifacts. Within a measurable constant of proportionality, the echo strain map can then be used at step 38 to estimate the spatially-dependent temperature rise between frames $F_1$ and $F_2$.

The present invention provides several advantages over prior methods for strain estimation used in pulse-echo ultrasound temperature measurements. For example, the present invention is more efficient due to its relative simplicity, since single-filter operations may be performed on entire two-dimensional frames at once, rather than on numerous individually windowed signals as is the current practice. As a result, the present invention may be easily implemented for real-time measurement of anatomical tissue, using, for example, standard digital signal processing ("DSP") circuitry. In addition, the present invention provides temperature information having fewer artifacts and improved accuracy as compared to present methods.

Figure 5:
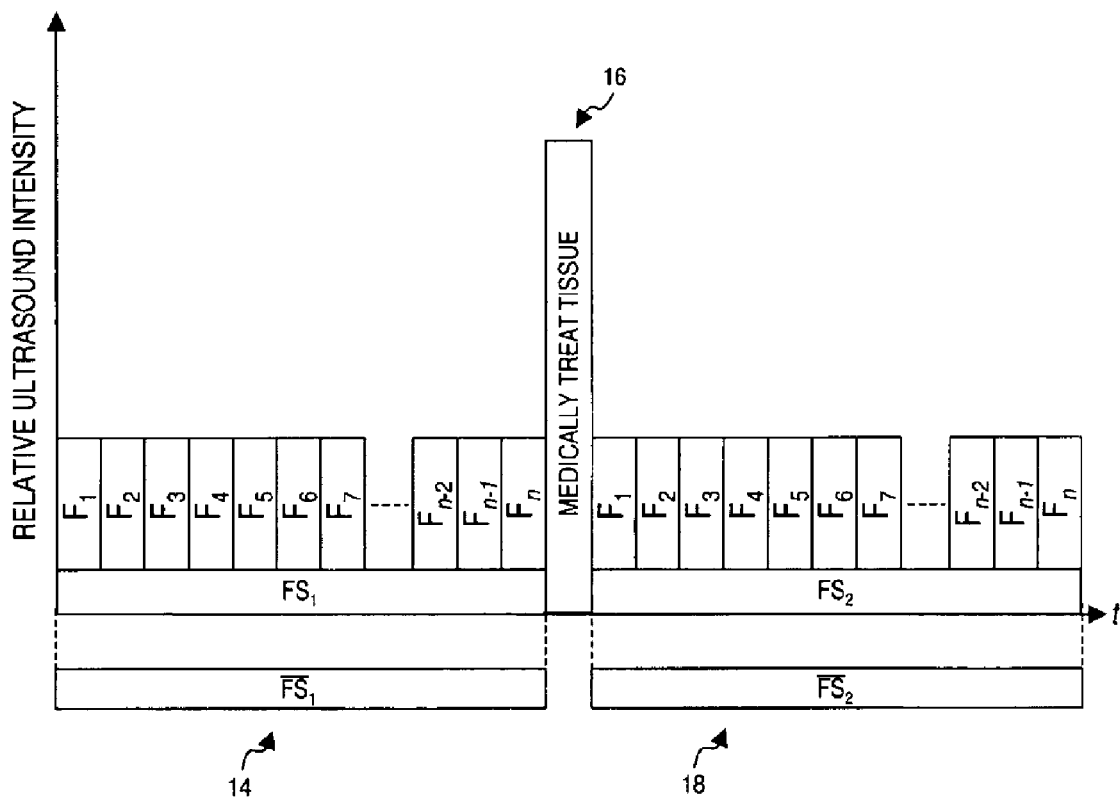
FIG. 5 depicts the relative amplitude and timing of ultrasound image frames and ultrasound treatments according to an alternate embodiment of the present invention.

In a first alternate embodiment, multiple frames may be grouped together as a "frame set." A diagram of the relative amplitude and timing of ultrasound image frame sets and ultrasound treatments is depicted in FIG. 5. Frame sets $FS_1$ and $FS_2$ may be averaged prior to computing the conjugate product. In this embodiment the method of FIG. 4 may be utilized with minor modification wherein $\overline{FS}_1$, the average of the signals of the frames comprising frame set $FS_1$, is substituted for $F_1$ of step 14. Likewise, $\overline{FS}_2$, the average of the signals of the frames comprising frame set $FS_2$, is substituted for $F_2$ of step 18. The resulting estimated temperature rise of step 38 contains a reduced number of uncertainties and artifacts as compared to the method of FIG. 4 using single frames.

Figure 6:
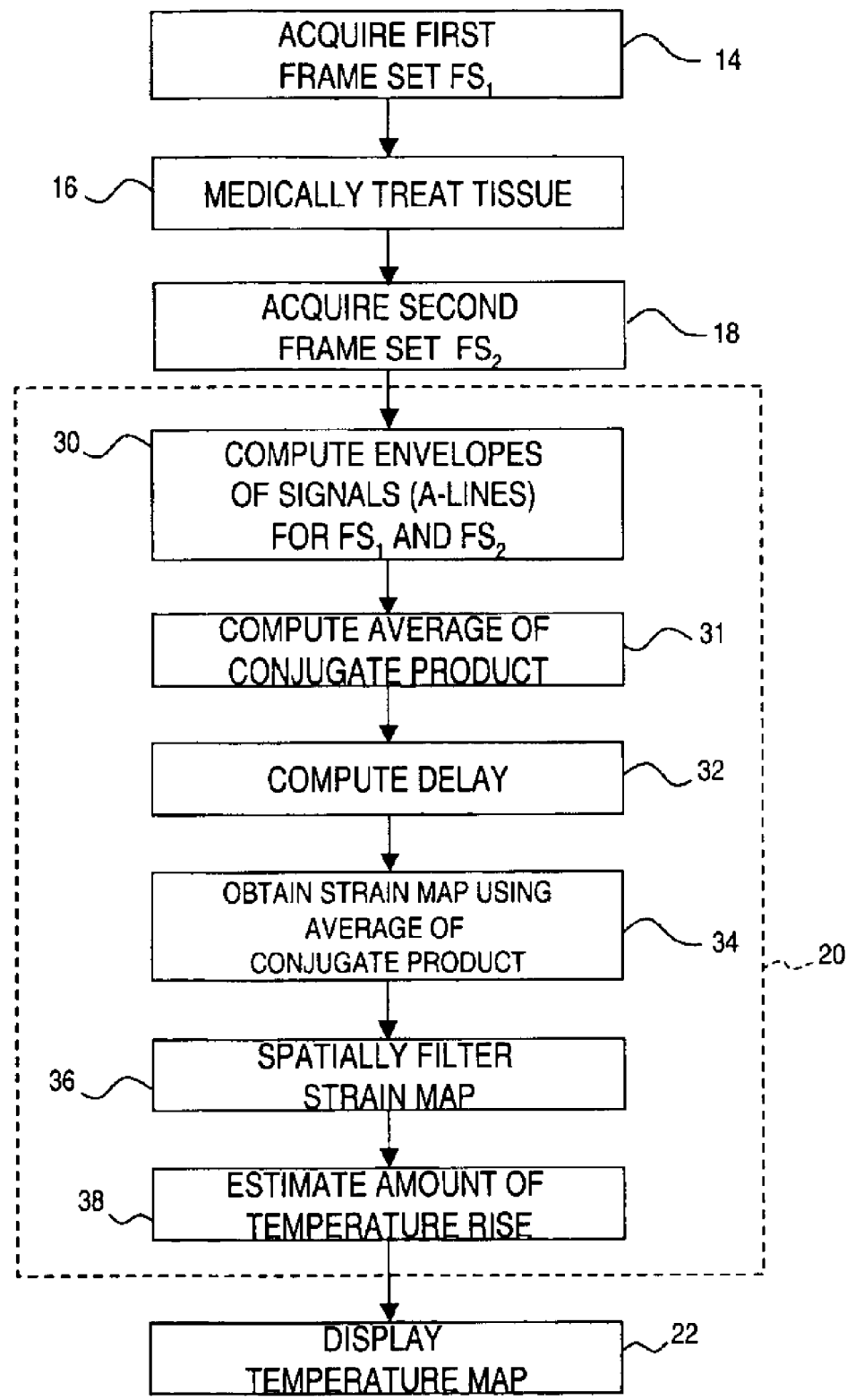
FIG. 6 is a flow diagram of a method for mapping temperature rise using pulse-echo ultrasound according to an alternate embodiment of the present invention.

In a second alternate embodiment, the present invention may include averaging of echo conjugate products from multiple frames before computing and differentiating the phase map to obtain the echo strain map. A method according to this embodiment is illustrated by FIG. 5 in combination with FIG. 6. An ultrasound transducer is positioned proximate the anatomical tissue, then at step 14 a first image frame set $FS_1$ is acquired. The tissue may then be medically treated such as by hyperthermia or ablating it with high-intensity ultrasound waves, as at step 16. A second image frame set $FS_2$ is then acquired at step 18. The raw echo signals of frame sets $FS_1$ and $FS_2$ may be processed at step 30, such as to obtain complex analytic signals by means of a Hilbert transformation, as previously disclosed. At step 31 an average of the conjugate products of step 30 is calculated. The average may be computed, for example, by computing and then averaging echo conjugate products of:

$F_1$ of $FS_1$ and $F_1$ of $FS_2$;

$F_2$ of $FS_1$ and $F_2$ of $FS_2$;

$F_1$ of $FS_1$ and $F_1$ of $FS_2$;

and so on. The delay is computed at step 32, then at step 34 an echo strain map is generated using the averaged conjugate products. The resulting echo strain map is then spatially filtered at step 36, the temperature rise is estimated at 38, and the temperature map is displayed at 22, all in the manner previously detailed. The averaged conjugate products serve to reduce uncertainties and artifacts in the estimated temperature maps as compared to the method of FIG. 4 using single frames.

In a third alternate embodiment, a correlation coefficient may be computed by multiplying one of the complex frames by a phase compensation function $e^{-i\theta}$, where $\theta$ is the low-pass filtered phase of the conjugate product. The normalized sum of the phase-corrected conjugate product is then a correlation coefficient whose amplitude indicates the reliability of the temperature estimation. Windowed sums, which can be implemented using known fast Fourier transform operations, provide a spatial map of the correlation coefficient. High values (i.e., values approaching 1) correspond to a high confidence in the temperature estimate, while values significantly less than 1 correspond to lower confidence. Estimated temperature maps can then be formed using higher-confidence estimates preferentially.

In a fourth alternate embodiment of the present invention, the echo conjugate product can be computed using a two-dimensional filtering operation, in which a two dimensional (i.e., azimuth/array and depth/time directions) window is used instead of the one-dimensional window described above for the third alternate embodiment. This method of computing the conjugate product will result in smoother strain maps, and thus may reduce artifacts in the temperature images.

In a fifth alternate embodiment of the present invention, the assumed relationship between echo strain and temperature rise may be non-linear rather than the linear relationship currently assumed. Such a non-linear relationship may be derived from measurements of the non-linear relationships between temperature, sound speed, and thermal expansion. The non-linear relationship may also be obtained empirically from calibration measurements in tissues of interest.

In a sixth alternate embodiment of the present invention, smoothing of strain maps may be enhanced by performing a thresholding operation before low-pass filtering. For example strain values above a predetermined temperature range of interest may be clipped. In this manner, artifactual strain peaks may be removed more effectively than by low-pass filtering alone.

Figure 7:
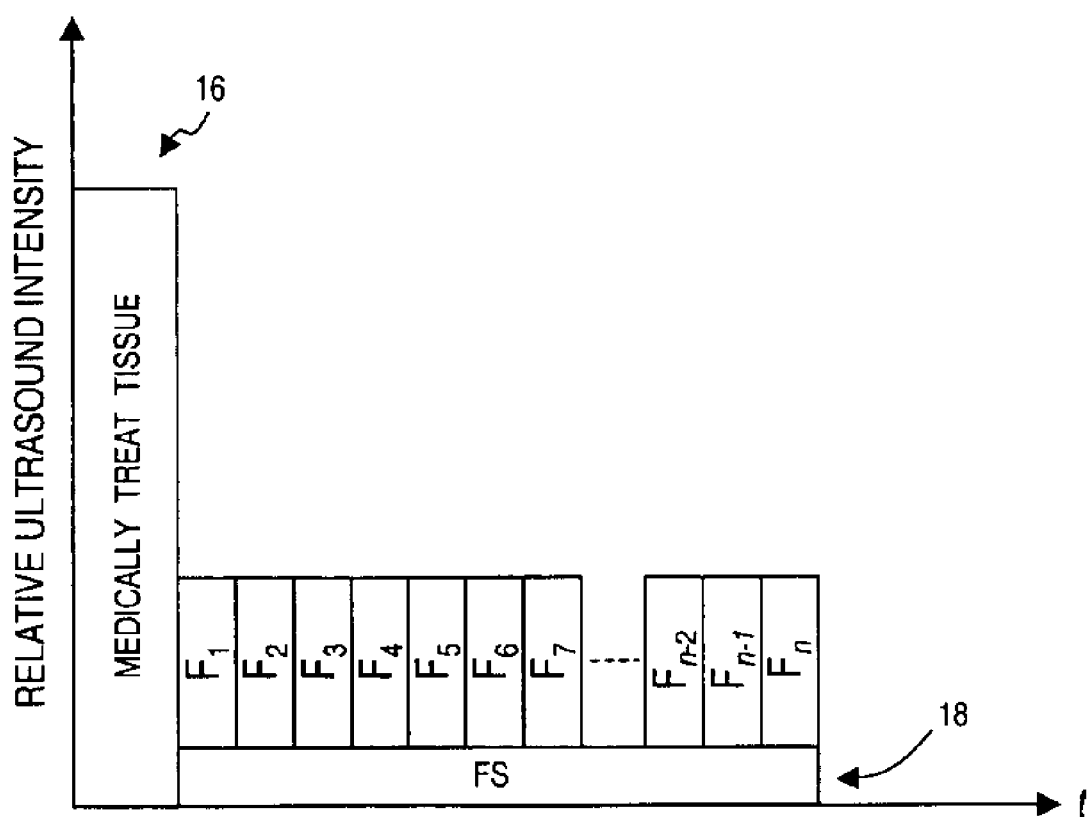
FIG. 7 shows the relative amplitude and timing of ultrasound image frames according to another alternate embodiment of the present invention.
Figure 8:
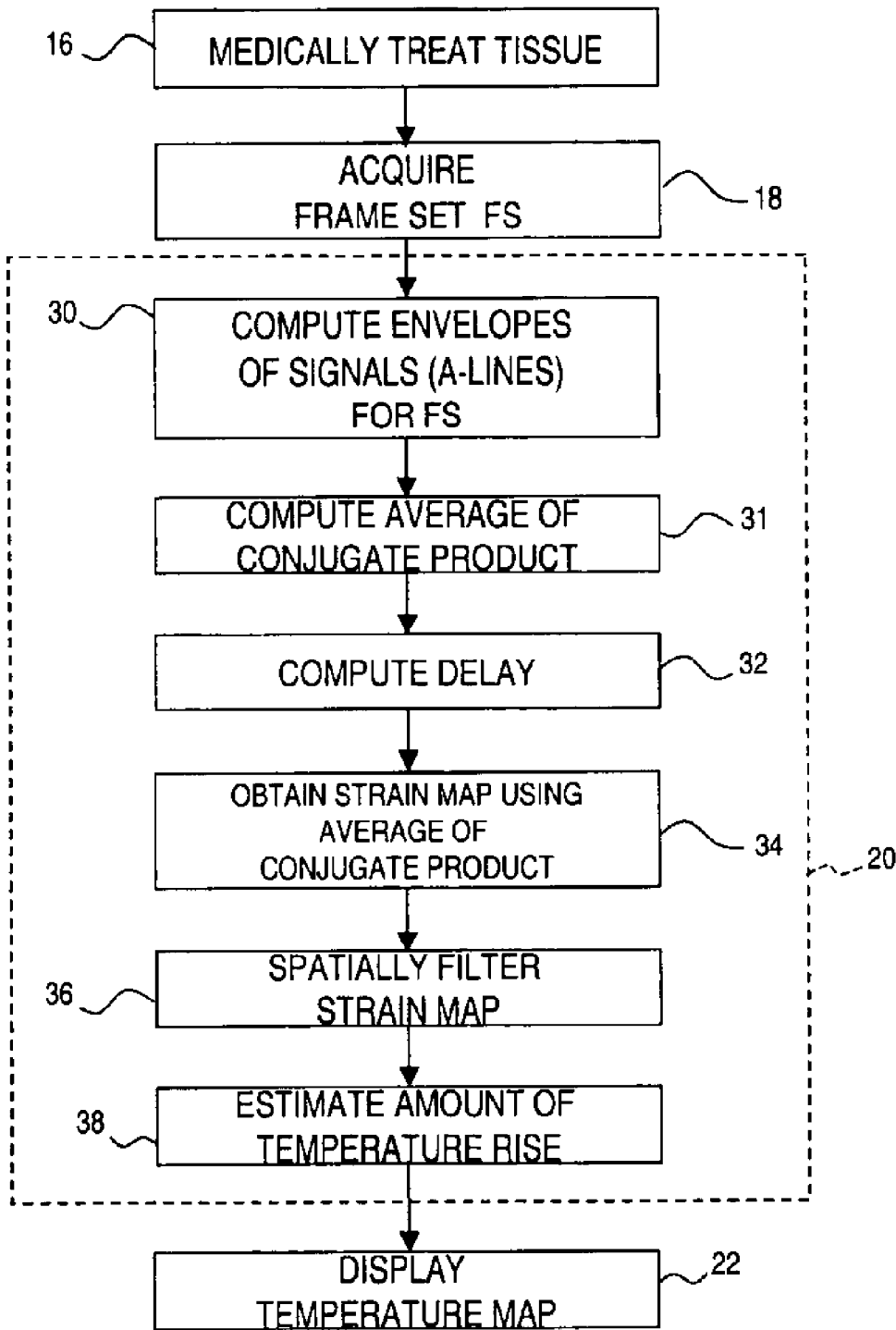
FIG. 8 depicts a flow diagram providing an overview of an ultrasound treatment method according to another embodiment of the present invention.

With reference to FIGS. 7 and 8, in a seventh alternate embodiment of the present invention, the conjugate products of adjacent frames of a frame set FS may be obtained, computed and averaged. At step 16 the tissue is medically treated such as by hyperthermia or ablating it with high-intensity ultrasound waves. An image frame set FS is then acquired at step 18. The raw echo signals of frames $F_1$–$F_n$ may be processed at step 30, such as to obtain complex analytic signals by means of a Hilbert transformation, as previously disclosed. At step 31 an average of the conjugate products of step 30 is calculated. The average may be computed, for example, by computing and then averaging echo conjugate products of adjacent frames, i.e.:

$F_1$ and $F_2$ of FS;

$F_2$ and $F_3$ of FS;

$F_3$ and $F_4$ of FS;

and so on. The delay is computed at step 32, then at step 34 an echo strain map is generated using the averaged conjugate products. The resulting echo strain map has reduced noise and artifactual content as compared to other imaging methods. The echo strain map is spatially filtered at step 36, the temperature change is estimated at 38, and the temperature map is displayed at 22, all in the manner previously detailed. The temperature change occurring in the time interval separating adjacent time frames may thus be estimated and displayed.

Figure 9:
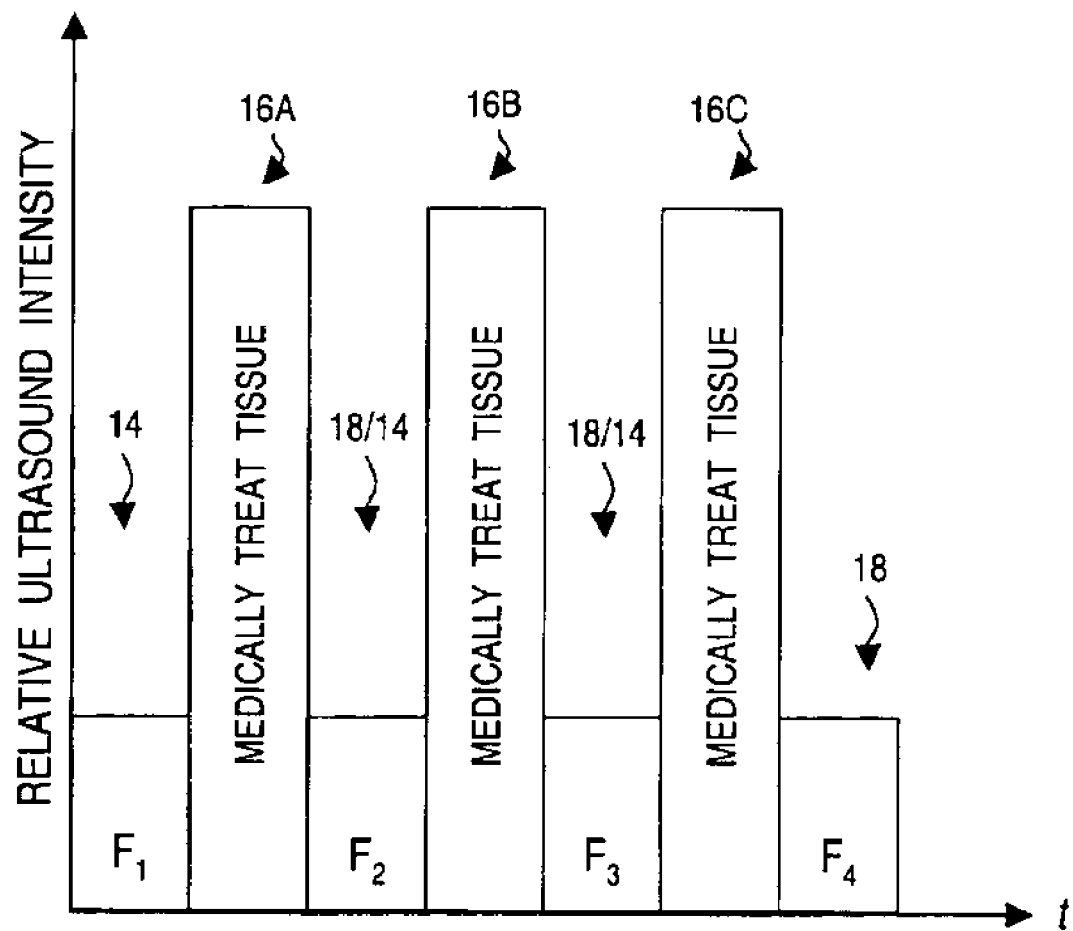
FIG. 9 illustrates the relative amplitude and timing of ultrasound image frames and ultrasound treatments of the method of FIG. 8.

In an eighth alternate embodiment of the present invention the steps of the method of FIG. 2 may be generally followed for a series of medical treatments 16, shown as 16A–16C in FIG. 9. A pre-treatment image frame $F_1$ is obtained at step 14 prior to the first treatment 16A. A post-treatment frame $F_2$ is then obtained at step 18 and used with the pre-treatment image $F_1$ to compute at step 20 the temperature change due to treatment 16A. A temperature map is displayed at step 22. Frame $F_2$ also serves as a pre-treatment image 14 for a subsequent treatment 16B, as shown in FIG. 9. Likewise, frame $F_3$ is a post-treatment frame for treatment 16B and is also a pre-treatment frame for treatment 16C. Finally, frame $F_4$ is a post-treatment image for treatment 16C. This process of imaging and treatment may be repeated as many times as desired. Further, the temperature change at 20 may be computed using any conventional mathematical function as previously discussed, such as averaging of frame images and averaging of the computed temperature change.

The foregoing description of several expressions of embodiments and methods of the invention has been presented for purposes of illustration. It is not intended to be exhaustive or to limit the present invention to the precise forms and procedures disclosed, and obviously many modifications and variations are possible in light of the above teaching. It is intended that the scope the invention be defined by the claims appended hereto.

What is claimed is:

1. A method for mapping temperature rise of anatomical tissue using pulse-echo ultrasound, comprising the steps of:
   a) obtaining a first signal of a first imaging ultrasound wave which has been reflected back from a region in the anatomical tissue at a first time;
   b) obtaining a second signal of a second imaging ultrasound wave which has been reflected back from the region in the anatomical tissue at a later second time wherein the tissue has received at least some medical treatment by the second time;
   c) computing first and second complex analytic signals from the first and second imaging signals;
   d) computing the depth-dependent delay from the conjugate product of the first and second analytic signals;
   e) generating an echo strain map from the slope of the depth-dependent delay;
   f) using the echo strain map to estimate the amount of temperature rise from the first imaging signal to the second imaging signal; and
   g) creating an image showing where temperature rise is occurring in the anatomical tissue.

2. The method of claim 1, further comprising the step of spatially filtering the difference signal.

3. The method of claim 2, further including the step of performing a thresholding operation to remove artifactual strain peaks.

4. The method of claim 1, further including the step of multiplying a signal of an ultrasound imaging wave by a phase compensation function to compute a correlation coefficient indicating the reliability of the temperature estimation.

5. The method of claim 4 wherein the signal is the first imaging signal.

6. The method of claim 5 wherein the signal is the second imaging signal.

7. The method of claim 4, further including the step of implementing windowed sums to provide a spatial map of the correlation coefficient.

8. The method of claim 7 wherein the windowed sums are two-dimensional.

9. The method of claim 1, wherein the echo strain map representing the slope of the depth-dependent delay assumes a linear relationship between echo strain and temperature rise.

10. The method of claim 1, wherein the echo strain map representing the depth-dependent delay assumes a non-linear relationship between echo strain and temperature rise.

11. The method of claim 10 wherein the non-linear relationship is derived from measurements of non-linear relationships between temperature, sound speed and thermal expansion.

12. The method of claim 10 wherein the non-linear relationship is derived empirically from calibration measurements in the anatomical tissue.

13. The method of claim 1, wherein the medical treatment is ultrasound medical treatment.

14. The method of claim 1, also including steps a) through g) for different regions to image the anatomical tissue, wherein the image includes medically-treated and medically-untreated regions of the anatomical tissue.

15. A method for mapping temperature rise of anatomical tissue using pulse-echo ultrasound, comprising the steps of:
   a) obtaining a first set of frames comprising a plurality of imaging ultrasound wave signals which have been reflected back from a region in the anatomical tissue during a first period of time;
   b) obtaining a second set of frames comprising a plurality of imaging ultrasound wave signals which have been reflected back from a region in the anatomical tissue at a later second time wherein the tissue has received at least some medical treatment by the second time;
   c) averaging together the signals of the first set of frames to obtain an averaged first imaging signal;
   d) averaging together the signals of the second set of frames to obtain an averaged second imaging signal;
   e) computing first and second complex analytic signals from the first and second averaged imaging signals;
   f) computing the depth-dependent delay from the conjugate product of the first and second analytic signals;
   g) generating a strain map from the slope of the depth-dependent delay;
   h) using the echo strain map to estimate the amount of temperature rise from the first averaged imaging signal to the second averaged imaging signal; and
   i) creating an image showing where temperature rise is occurring in the anatomical tissue.

16. The method of claim 15, further comprising the step of spatially filtering the difference signal.

17. The method of claim 15, wherein the medical treatment is ultrasound medical treatment.

18. The method of claim 15, also including steps a) through i) for different regions to image the anatomical tissue, wherein the image includes medically-treated and medically-untreated regions of the anatomical tissue.

19. A method for mapping temperature rise of anatomical tissue using pulse-echo ultrasound, comprising the steps of:
   a) obtaining a first set of frames comprising a plurality of imaging ultrasound wave signals which have been reflected back from a region in the anatomical tissue during a first period of time;

b) obtaining a second set of frames comprising a plurality of imaging ultrasound wave signals which have been reflected back from a region in the anatomical tissue at a later second time wherein the tissue has received at least some medical treatment by the second time;

c) computing complex analytic signals from a selected frame from the first set of frames and a selected frame from the second set of frames;

d) computing the conjugate product of the complex analytic signals of step c);

e) repeating steps c) and d) until conjugate products have been computed for all of the frames of the first and second frame sets;

f) computing the average of the conjugate products of step e);

g) computing the depth-dependent delay from the averaged conjugate product of step f);

h) generating an echo strain map from the slope of the depth-dependent delay;

i) using the echo strain map to estimate the amount of temperature rise from the first averaged imaging signal to the second averaged imaging signal; and j) creating an image showing where temperature rise is occurring in the anatomical tissue.

20. A method for mapping temperature change in anatomical tissue using pulse-echo ultrasound, comprising the steps of:

a) obtaining a set of frames comprising a plurality of imaging ultrasound wave signals which have been reflected back from a region in the anatomical tissue during a period of time;

b) computing complex analytic signals from the set of frames;

c) computing the conjugate product of a pair of adjacent frames of the set of frames;

d) repeating step c) until the conjugate products of all adjacent frames have been computed;

e) averaging the conjugate products of the adjacent frames of step d);

f) computing a depth-dependent delay map from the average conjugate product;

g) generating an echo strain map from the slope of the depth-dependent delay;

h) using the echo strain map to estimate the amount of temperature change from the first frame to the second frame; and i) creating an image showing where temperature change is occurring in the anatomical tissue.

21. A method for mapping temperature rise of anatomical tissue using pulse-echo ultrasound, comprising the steps of:

a) obtaining a first signal of a first imaging ultrasound wave which has been reflected back from a region in the anatomical tissue at a first time;

b) obtaining a second signal of a second imaging ultrasound wave which has been reflected back from the region in the anatomical tissue at a later second time wherein the tissue has received at least some medical treatment by the second time;

c) computing first and second complex analytic signals from the first and second imaging signals;

d) computing the depth-dependent delay from the conjugate product of the first and second analytic signals;

e) generating an echo strain map from the slope of the depth-dependent delay;

f) using the echo strain map to estimate the amount of temperature rise from the first imaging signal to the second imaging signal;

g) creating an image showing where temperature rise is occurring in the anatomical tissue; and h) repeating the method at least once by:
   i) re-defining the second imaging signal obtained at step b) as the first imaging signal of step a);
   ii) obtaining a new second imaging signal at step b); and
   ii) repeating steps c) through g).

* * * * *

UNITED STATES PATENT AND TRADEMARK OFFICE
CERTIFICATE OF CORRECTION

PATENT NO.        : 7,211,044 B2
APPLICATION NO.   : 10/735045
DATED             : May 1, 2007
INVENTOR(S)       : T. Douglas Mast and Waseem Faidi It is certified that error appears in the above-identified patent and that said Letters Patent is hereby corrected as shown below:

Title page, Item (75) Inventors should include after last named inventor:

Inder Raj S. Makin, Loveland, Ohio (US);
Peter G. Barthe, Phoenix, AZ (US);
Michael H. Slayton, Tempe, AZ (US)

Signed and Sealed this

Fifteenth Day of December, 2009

David J. Kappos
*Director of the United States Patent and Trademark Office*